United States Patent [19]

Coy et al.

[11] Patent Number: 4,485,101

[45] Date of Patent: Nov. 27, 1984

[54] PEPTIDES

[75] Inventors: David H. Coy; William A. Murphy, both of New Orleans, La.

[73] Assignee: Administrators of the Tulane Educational Fund, New Orleans, La.

[21] Appl. No.: 540,380

[22] Filed: Oct. 11, 1983

[51] Int. Cl.$^3$ .................... A61K 37/00; C07C 103/52
[52] U.S. Cl. .............................. 424/177; 260/112.5 S
[58] Field of Search .................. 260/112.5 S; 424/177

[56] References Cited

U.S. PATENT DOCUMENTS

| | | | |
|---|---|---|---|
| 4,133,782 | 1/1979 | Vale, Jr. et al. | 260/112.5 S |
| 4,190,575 | 2/1980 | Sarantakis | 260/112.5 S |
| 4,209,426 | 6/1980 | Sarantakis | 260/112.5 S |
| 4,211,693 | 7/1980 | Rivier et al. | 260/112.5 S |
| 4,215,039 | 7/1980 | Sarantakis | 260/112.5 S |
| 4,224,199 | 9/1980 | Meyers et al. | 260/112.5 S |
| 4,369,179 | 1/1983 | Rink et al. | 260/112.5 S |

OTHER PUBLICATIONS

Hirst, B. H., (1980), Regulatory Peptides, 1, 97–113.

Primary Examiner—Delbert R. Phillips

[57] ABSTRACT

In one aspect, dodecapeptides capable of inhibiting GH, insulin, and glucagon secretion and having the formula N-acetyl-Cys-Lys-Asn-A-Phe-D-Trp-Lys-Thr-Phe-Thr-Ser-B-NH$_2$ wherein A is Phe or 4-X-Phe wherein X is Cl, Br, or F, and B is Cys or D-Cys; or a pharmaceutically acceptable salt thereof.

12 Claims, No Drawings

PEPTIDES

BACKGROUND OF THE INVENTION

This invention relates to therapeutic peptides.

A number of somatostatin analogs exhibiting GH-release-inhibiting activity have been described. For example, Vale et al. U.S. Pat. No. 4,133,782 describes various somatostatin analogs in which the eighth amino acid can be D-Trp, rather than the naturally occurring L-Trp, and the fourteenth amino acid can be D-Cys instead of Cys. (Hereinafter, when no designation of configuration is given, the L-form is meant).

Hirst et al. (1980) Regulatory Peptides 1, 97, describes somatostatin analogs in which the eighth amino acid can be (L or D)-5F-Trp and the fourteenth amino acid can be D-Cys.

Meyers et al. U.S. Pat. No. 4,224,199 describes somatostatin analogs in which the eighth amino acid can be (L or D)-5X-Trp, where X is F or Br.

SUMMARY OF THE INVENTION

In general, in one aspect, the invention features a dodecapeptide of the formula:

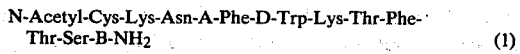

N-Acetyl-Cys-Lys-Asn-A-Phe-D-Trp-Lys-Thr-Phe-Thr-Ser-B-NH$_2$     (1)

wherein A is Phe or 4-X-Phe wherein X is Cl, Br, or F, and B is Cys or D-Cys; its cyclic 1-12 disulfide analog; or a pharmaceutically acceptable salt thereof.

In another aspect the invention features a tetradecapeptide of the formula

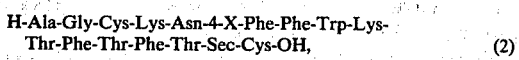

H-Ala-Gly-Cys-Lys-Asn-4-X-Phe-Phe-Trp-Lys-Thr-Phe-Thr-Phe-Thr-Sec-Cys-OH,     (2)

wherein X is Cl, Br, or F; its cyclic 3-14 disulfide analog; or a pharmaceutically acceptable salt thereof.

In preferred embodiments of the dodecapeptide, A is 4-Cl-Phe while B is Cys; or A is 4-Cl-Phe while B is D-Cys.

In a preferred embodiment of the tetradecapeptide, X is Cl.

In other preferred embodiments, a therapeutically effective amount of the therapeutic compound and a pharmaceutically acceptable carrier substance, e.g. magnesium carbonate or lactose, together form a therapeutic composition, e.g. a pill, tablet, capsule, or liquid for oral administration to a human patient, a spreadable cream, gel, lotion, or ointment for application to the skin of a human patient in need of the compound, a liquid capable of being administered nasally as drops or spray, or a liquid capable of intravenous, parenteral, subcutaneous, or intraperitoneal administration. The pill, tablet, or capsule can be coated with a substance capable of protecting the composition from the gastric acid in the patient's stomach for a period of time sufficient to allow the composition to pass undisintegrated into the patient's small intestine.

The compounds of the invention are active in inhibiting the secretion of GH, insulin, and glucagon. Furthermore, the structure of the dodecapetide can be controlled to provide more or less specific inhibitory activity against the target hormones glucagon and insulin. For example, Cys at position 12 provides high inhibitory activity against all three hormones, while D-Cys at position 12 provides selectively greater inhibition of glucagon and insulin. Dodecapeptides having 4-Cl-Phe at position 4 have a longer biological half life than does somatostatin.

Other features and advantages of the invention will be apparent from the following description of the preferred embodiments thereof, and from the claims.

DESCRIPTION OF THE PREFERRED EMBODIMENTS

We turn now to a description of preferred embodiments of the invention.

Structure

The compounds of the invention have either of the two general formulae recited in the Summary of the Invention above. The compounds can exist either as the straight chain peptides shown in Formulae 1 and 2 or as the corresponding 1-12 or 3-14 disulfide cyclic analogs. Examples of preferred compounds within the general formulae are those referred to as preferred embodiments above.

The dodecapeptides all have an acetyl group at the amino terminal end and an NH$_2$ at the carboxy terminal end. In addition, they all have a D-Trp at position 6 and the Phe at position 4 is halogenated. The tetradecapeptides are all analogs of somatostatin in which the Phe at position 6 is halogenated.

The compounds can be provided in the form of pharmaceutically acceptable salts. Examples of preferred salts are those with therapeutically acceptable organic acids, e.g., acetic, lactic, maleic, citric, malic, ascorbic, succinic, benzoic, salicylic, methanesulfonic, toluenesulfonic, or pamoic acid, as well as polymeric acids such as tannic acid or carboxymethyl cellulose, and salts with inorganic acids such as the hydrohalic acids, e.g., hydrochloric acid, sulfuric acid, or phosphoric acid.

Synthesis

The synthesis of

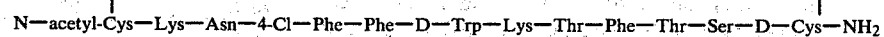

N—acetyl-Cys—Lys—Asn—4-Cl—Phe—Phe—D—Trp—Lys—Thr—Phe—Thr—Ser—D—Cys—NH$_2$

D-Cys.

follows.

Other dodecapeptides and tetradecapeptides of the invention can be prepared by making appropriate modifications, within the ability of someone of ordinary skill in this field, of the following synthetic method.

The first step is the preparation of N-acetyl-S-methyl-benzyl-L-Cys-Nε-4-chlorobenzyloxycarbonyl-Lys-Asn-4-Cl-Phe-Phe-D-Trp-Nε-4-chlorobenzyloxycarbonyl-Lys-O-benzyl-Thr-Phe-O-benzyl-Thr-O-benzyl-Ser-S-4-methylbenzyl-Cys-benzydrylamine resin, as follows.

Benzyhydrylamine polystyrene resin (Bachem, Inc., Torrance, CA) (1.58 g, 0.50 mmol) in the chloride ion form is placed in the reaction vessel of a Beckman 990 Model 990 automatic peptide synthesizer programmed to carry out the following work-wash cycle:

(a) CH$_2$Cl$_2$; (b) 33% trifluoroacetic acid in CH$_2$Cl$_2$ (2 times for 1 hr. and 25 min each); (c) CH$_2$Cl$_2$; (d) C$_2$H$_5$OH; (e) CH$_2$Cl$_2$; (f) 10% (C$_2$H$_5$)$_3$N in CHCl$_3$ (2 times for 2 min each); and (g) CH$_2$Cl$_2$.

The neutralized resin is stirred with alpha-t-butyloxycarbanonyl(Boc)-S4-methylbenzyl-cysteine [Boc-Cys(MeBzl)]and diisopropylcarbodiimide (3 mmol) in CH$_2$Cl$_2$ for 1 hour and the resulting amino acid resin is then cycled through the steps (a) through (g) in the above wash program. The following amino acids (3 mmol) are then coupled successively by the same reaction cycle: Boc-Ser(Bzl),Boc-Thr(Bzl), Boc-Phe, Boc(Thr(Bzl), Boc-Lys(Cl-Z), Boc-D-Trp, Boc-4-Cl-Phe, Boc-Phe, Boc-Asn, Boc-Lys (Cl-Z), Boc-Cys(-MeBzl), except that Boc-Asn is coupled in the presence of 1-hydroxybenzotriazole (3 mmol) in dimethylformamide solution.

The completed peptide-benzyhydrylamine resin with the N-terminal Boc group removed is acetylated at the free N-amino group by treatment with 10% acetic anhydride-(C$_2$H$_5$)$_3$N in CH$_2$Cl$_2$ for 15 min. The resin is then washed with CH$_3$OH and air dried.

From the above resin is prepared the desired dodecapeptide product, i.e. the cyclic 1–12 disulfide of N-acetyl-Cys-Lys-Asn-4-Cl-Phe-Phe-D-Trp-Lys-Thr-Phe-Thr-Ser-Cys-NH$_2$, as follows.

A mixture of the above dodecapeptide resin (1.04 g) and a solution of 10% anisole and 100 mg of dithiothreitol in hydrogen fluoride (37 ml) is stirred at 0° C. for 1 hour. Excess hydrogen fluoride is evaporated rapidly under a stream of dry nitrogen and the resin and free peptide are washed free of anisole with a large volume of ethyl acetate.

The peptide is then extracted into 500 ml of 90% acetic acid/water and cyclized via the cysteine residues by the dropwise addition of 10% iodine in methanol until a permanent brown color is obtained. The mixture is then stirred for 1 hour and excess iodine removed by addition of zinc powder.

The filtered solution is reduced to a small volume in vacuo and loaded onto a column (2.5×95 cm) of Sephadex G-15 which is eluted with 50% acetic acid in water. Fractions containing a major peak observed at 280 nm are pooled and evaporated to a small volume in vacuo. This solution is applied to a column (2.5×45 cm) of octadecylsilane-silica (Whatman LRP-1, 15–20 μM mesh size) which is eluted with a linear gradient of 15–35% acetonitrile in 20% acetic acid-water. Fractions containing a major peak are examined by hplc and tlc and pooled to give maximum purity. Lyophilization of the solution gives 25 mg of the product as a fluffy white powder.

This material is found to be homogeneous by analytical hplc on octadecylsilane-silica (Vydac 5 μM, 0.4×25 cm) eluted with an acetonitrile/0.1% trifluoroacetic acid-water system and by tlc in 4 solvent systems on silica gel plates. Amino acid analysis of an acid hydrolysate gives the following expected amino acid ratios: Cys, 1.78; Lys, 1.82; Asp, 1.05; Phe, 1.94; Trp, 0.88; 4-Cl-Phe, 0.91; Thr, 2.11; Ser, 0.83.

As mentioned above, other peptides of the invention can be prepared by appropriately modifying the above procedure. For example, to make a dodecapeptide of the invention having Phe rather than 4-Cl-Phe at position 4, the benzhydrylamine resin is prepared as above, substituting Phe for 4-Cl-Phe, and the resin is treated with hydrogen fluoride, as described, to yield the homogenous fluffy white powder having the formula N-acetyl-Cys-Lys-Asn-Phe-Phe-D-Trp-Lys-Thr-Phe-Thr-Ser-Cys-NH$_2$ product, of which the amino acid analysis of the acid hydrolysate gives the following expected amino acid ratios: Cys, 1.78; Lys, 1.87; Asp, 1.04; Phe, 2.85; Trp, 0.90; Thr, 2.09; Ser, 0.82.

In another dodecapeptide, in which there is D-Cys rather than Cys at position 12, the first step is to prepare the benzhydrylamine resin, as described, using D-Cys(-MeBzl) rather than Cys(MeBzl). The dodecapeptide product is then prepared via hydrogen fluoride treatment of the resulting resin peptide. The product is a homogeneous fluffy white powder having the formula N-acetyl-Cys-Lys-Asn-4-Cl-Phe-Phe-D-Trp-Lys-Thr-Phe-Thr-Ser-D-Cys-NH$_2$ which gives the following expected amino acid ratios: Cys, 1.80; Lys, 2.03; Asp, 1.05; Phe, 2.06; Trp, 0.91; 4-Cl-Phe, 0.91; Thr, 2.12; Ser; 0.92.

Use

When administered to mammals (e.g. orally, topically, intravenously, parenterally, nasally, or by suppository), the compounds can be effective to inhibit GH release as well as to inhibit insulin and glucagon.

The compounds can be administered to a mammal, e.g. a human, in the dosages used for somatostatin. The compounds of the invention can be used for the treatment of cancer (e.g., bone, cartilage, pancreas, prostate, or breast), acromegaly and related hypersecretory endocrine states, or of bleeding ulcers in emergency patients and in those suffering from pancreatitis or diarrhia. The compounds can also be used in the management of diabetes and to protect the liver of patients suffering from cirrhosis or hepatitis.

The compounds can be administered to a mammal, e.g., a human, in a dosage of 0.01 to 1000 mcg/kg/day, preferably 0.1 to 100 mcg/kg/day.

Other embodiments are within the following claims.

We claim:

1. A dodecapeptide of the formula: N-acetyl-Cys-Lys-Asn-A-Phe-D-Trp-Lys-Thr-Phe-Thr-Ser-B-NH$_2$ wherein A is Phe or 4-X-Phe wherein X is Cl, Br, or F, and B is Cys or D-Cys; its cyclic 1–12 disulfide analog; or a pharmaceutically acceptable salt thereof.

2. The dodecapeptide of claim 1 wherein A is 4-Cl-Phe and B is Cys; its cyclic 1–12 disulfide analog; or a pharmaceutically acceptable salt thereof.

3. The dodecapeptide of claim 1 wherein A is 4-Cl-Phe and B is D-Cys; its cyclic 1–12 disulfide analog; or a pharmaceutically acceptable salt thereof.

4. A therapeutic composition capable of inhibiting the release of growth hormone, insulin, or glucagon comprising a therapeutically effective amount of the compound of claim 1 together with a pharmaceutically acceptable carrier substance.

5. A method of treating a mammal in need of reduction of growth hormone, insulin, or glucagon secretion comprising administering to said mammal a therapeutically effective amount of the compound of claim 1.

6. The therapeutic composition of claim 4 wherein said composition is in the form of a pill, tablet, or capsule for oral administration to a human patient in need of said compound.

7. The therapeutic composition of claim 4 wherein said composition is in the form of a liquid for oral administration to a human patient in need of said compound.

8. The therapeutic composition of claim 6, said composition being coated with a substance capable of protecting said composition from the gastric acid in the stomach of said human patient for a period of time sufficient to allow said composition to pass undisintegrated into the small intestine of said human patient.

9. The therapeutic composition of claim 4, said composition being in the form of a cream, gel, spray, or ointment for application to the skin of a human patient in need of said compound.

10. The therapeutic composition of claim 4, said composition being in the form of a liquid capable of being administered nasally as drops or spray to a human patient in need of said compound.

11. The therapeutic composition of claim 4, said composition being in the form of a liquid for intravenous, subcutaneous, parenteral, or intraperitoneal administration to a human patient in need of said compound.

12. The dodecapeptide of claim 1 wherein A is Phe and B is Cys; its cyclic 1–12 disulfide analog; or a pharmaceutically acceptable salt thereof.

* * * * *

UNITED STATES PATENT AND TRADEMARK OFFICE
CERTIFICATE OF CORRECTION

PATENT NO. : 4,485,101
DATED : November 27, 1984
INVENTOR(S) : David H. Coy et al.

It is certified that error appears in the above-identified patent and that said Letters Patent is hereby corrected as shown below:

As a first sentence and paragraph, insert the paragraph:

--This invention was made in the course of work under a grant or award from the U.S. government; therefore, the U.S. government has rights in the invention.--

Signed and Sealed this

Twenty-fourth Day of December, 1991

Attest:

HARRY F. MANBECK, JR.

Attesting Officer     Commissioner of Patents and Trademarks